(12) United States Patent
Tan

(10) Patent No.: US 8,361,985 B2
(45) Date of Patent: Jan. 29, 2013

(54) SHORT HAIRPIN RNA FOR GENE KNOCKDOWN OF NR1 SUBUNIT OF THE N-METHYL-D-ASPARTATE RECEPTOR AND ITS APPLICATION ON PHARMACEUTICS

(75) Inventor: Ping-Heng Tan, Kaohsiung (TW)

(73) Assignee: I-Shou University, Kaohsiung (TW)

( * ) Notice: Subject to any disclaimer, the term of this patent is extended or adjusted under 35 U.S.C. 154(b) by 85 days.

(21) Appl. No.: 13/027,742

(22) Filed: Feb. 15, 2011

(65) Prior Publication Data

US 2012/0172410 A1    Jul. 5, 2012

(30) Foreign Application Priority Data

Dec. 30, 2010   (TW) .............................. 99146981 A

(51) Int. Cl.
*C12N 15/11*    (2006.01)
(52) U.S. Cl. .................................... 514/44 A
(58) Field of Classification Search ............. 514/44 A
See application file for complete search history.

(56) References Cited

U.S. PATENT DOCUMENTS

| | | | |
|---|---|---|---|
| 6,924,109 | B2 | 8/2005 | Melcher et al. |
| 7,399,586 | B2 | 7/2008 | Klinghoffer et al. |
| 7,667,028 | B2 | 2/2010 | Kremmidiotis et al. |
| 7,687,080 | B2 | 3/2010 | Wolicki |
| 7,691,999 | B2 | 4/2010 | McSwiggen et al. |
| 7,700,122 | B1 | 4/2010 | Kolesnikov et al. |
| 7,829,694 | B2 | 11/2010 | Kaemmerer |
| 7,858,771 | B2 | 12/2010 | McSwiggen et al. |

FOREIGN PATENT DOCUMENTS

TW    99107164    3/1999

OTHER PUBLICATIONS

Garraway et al. (The Journal of Pharmacology and Experimental Therapeutics, 2007, 322, 982-988).*
Garraway et al. (J. Pain Apr. 2009, 10:380-390).*
Miskevich et al. (Journal of Neuroscience Methods 152, 2006:65-73).*
Ping-Heng, Tan et al., "Gene knockdown of the N-methyl-D-aspartate receptor NR1 subunit with subcutaneous small interfering RNA reduces inflammation-induced nociception in rats." *Anesthesiology*, Jun. 2010., pp. 1482-1493, vol. 112 No. 6. Kaohsiung, TW.
Ping-Heng, Tan et al., "RNA interference-mediated gene silence of the NR1 subunit of the NDMA receptor by subcutaneous injection of vector-encoding short hairpin RNA reduces formalin-induced nociception in the rat." *Pain*, Nov. 26, 2010, pp. 1-9.

* cited by examiner

*Primary Examiner* — Brian Whiteman
(74) *Attorney, Agent, or Firm* — Muncy, Geissler, Olds & Lowe, PLLC

(57) ABSTRACT

A short hairpin RNA (shRNA) for gene knockdown the genetic expression of NR1 subunit of N-methyl-D-aspartate (NMDA) receptor comprises a first fragment sharing homologous nucleotides among the NR1 subunit of NMDA receptor; a second fragment having complementary sequence to the first fragment; and a connecting fragment having any base in repeated arrangement, and connecting to the first and second fragments. Also, a method of treatment for pathological pain, by applying the shRNA described above to subcutaneous tissues of living organisms for gene knockdown the genetic expression of the NR1 subunit of NMDA receptor in hypoderm.

12 Claims, 11 Drawing Sheets

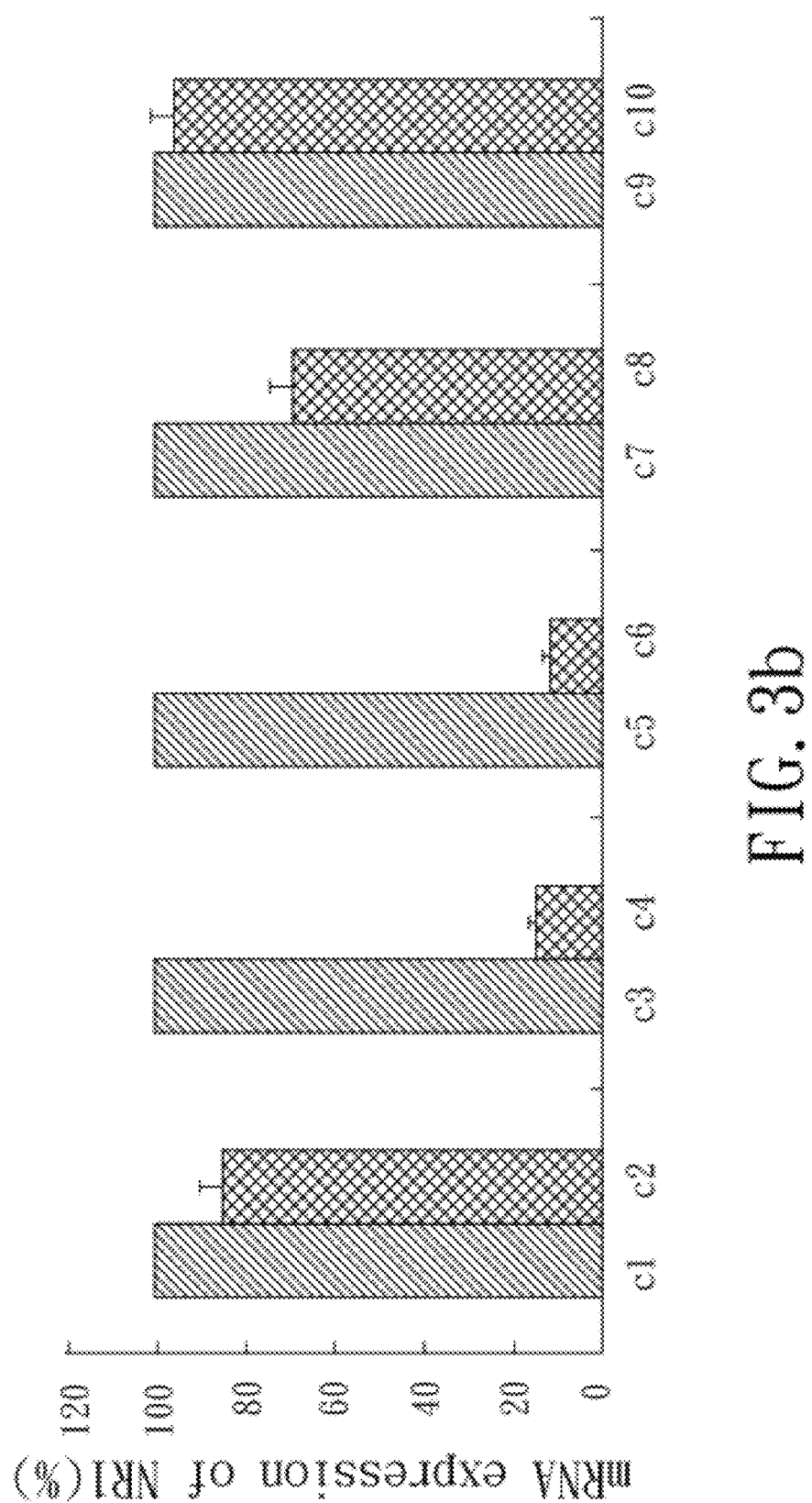

SHORT HAIRPIN RNA FOR GENE KNOCKDOWN OF NR1 SUBUNIT OF THE N-METHYL-D-ASPARTATE RECEPTOR AND ITS APPLICATION ON PHARMACEUTICS

BACKGROUND OF THE INVENTION

1. Field of the Invention

The present invention relates to a short hairpin RNA, and a medicament comprising the hairpin RNA, particularly to a hairpin RNA targeting to NR1 subunit of N-methyl-D-aspartate receptor, and an analgesic drug with the above hairpin RNA.

2. Description of the Related Art

In general, pain induced by skin injuries, like burn or scald, is very complex and intolerable. Serious skin injuries usually cause an extensive release of peripheral neurotransmitter for activating glutamate receptors, including N-methyl-D-aspartate (NMDA), α-amino-3-hydroxy-5-methylisoxazolone-4-propionic acid (AMPA) and kainite variants, which will turn on the mechanism of inflammatory pain and bring miserable pain to patients.

The NMDA receptors take important role in the central nervous system, and have been reported to involve in normal functions of central sensitization. Current reports suggest that the NMDA receptors located at sensory axons, as well as the general functions thereof, can be attenuated by localized delivery of a NMDA receptor antagonist. With such investment, the NMDA receptor antagonization provides an alternative approach of inflammatory pain treatment in clinical medicine.

With reference to Taiwan Patent Application No. 099107164, also known as U.S. patent application Ser. No. 12/780,278 and entitled with "A SMALL INTERFERING RNA FOR GENE KNOCKDOWN OF THE SUBCUTANEOUS N-METHYL-D-ASPARTATE RECEPTOR NR1 SUBUNIT AND ITS APPLICATION ON PHARMACEUTICS", a small interfering RNA (siRNA) is synthesized and applied to clinical treatment of inflammatory pain. By subcutaneous injection of the siRNA, neither the mRNA, nor the protein of the NR1 subunit of NMDA receptors can normally express. As a result, the inflammatory pain on skin-injured patients will be effectively relieved.

However, siRNAs have unstable double-stranded structure, being easily and rapidly degradable after delivery into living organisms. The limitation of the synthetic siRNAs-mediated RNA interference (RNAi) in cells is that it is a transient effect, with the cells rapidly recovering from a single treatment. It emerges that the siRNAs of the conventional invention is limited to achieve long-term gene silencing and a long-period of analgesia. Hence, an alternative approach is needed for improving the shortage of the siRNAs of the conventional invention, and providing long-term gene silencing and antinociception.

SUMMARY OF THE INVENTION

The primary objective of this invention is to provide a short hairpin RNA (shRNA) for gene knockdown of NR1 subunit of N-methyl-D-aspartate receptor, which provides long-term suppression on the NR1 subunit of NMDA receptor.

The secondary objective of this invention is to provide a method of treatment for pathological pain by singly delivering a small dosage of shRNA in hypoderm to achieve a long-term inhibition of the NR1 expression, as well as the normal functions thereof.

Another objective of this invention is to provide an analgesic with shRNA for skin inflammation pain, which provides persistent effect on pain relief.

A shRNA comprises a first fragment sharing homologous nucleotides among NR1 subunit of N-methyl-D-aspartate (NMDA) receptor for gene knockdown the genetic expression of NR1 subunit; a second fragment having complementary sequence to the first fragment; and a connecting fragment having any base in any arrangement and being connecting to the first and second fragments.

An analgesic drug for skin inflammation pain comprises a shRNA as it is described above and an acceptable vehicle for the shRNA.

A method of treatment for pathological pain, characterized by applying the above shRNA to subcutaneous tissues of living organisms for temporary knockdown the genetic expression of NR1 subunit of NMDA receptor in hypoderm.

Further scope of the applicability of the present invention will become apparent from the detailed description given hereinafter. However, it should be understood that the detailed description and specific examples, while indicating preferable embodiments of the invention, are given by way of illustration only, since various will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention, and wherein:

FIG. 3b is a bar chart illustrating mRNA expression of NR1 in rats after subcutaneous injection of NR1 shRNA;

In the various figures of the drawings, the same numerals designate the same or similar parts.

DETAILED DESCRIPTION OF THE INVENTION

Figure 1A:
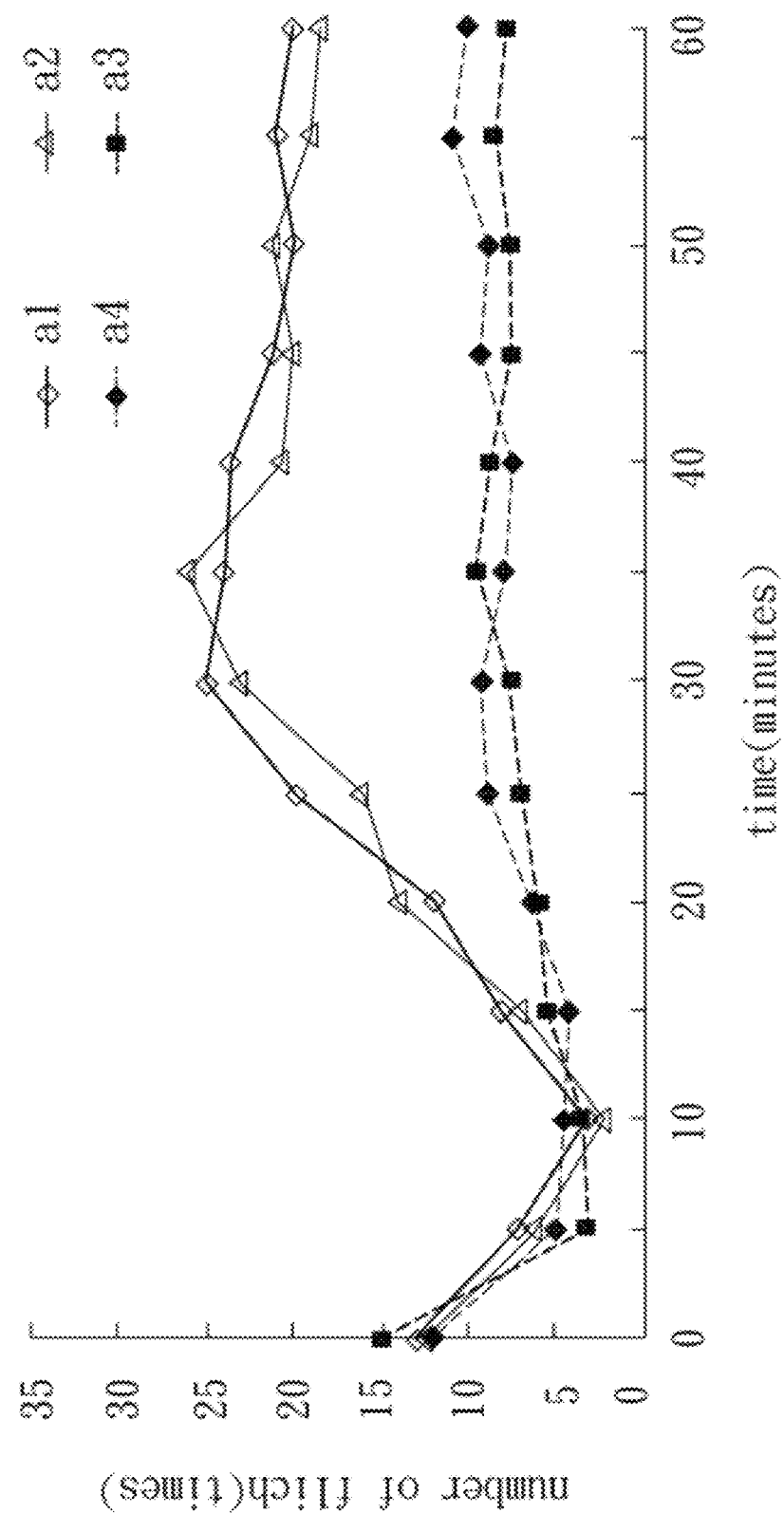
FIG. 1a is a line chart illustrating data of flinches response in rats on formalin-induced nociception.

With reference to GenBank, a shRNA of the present invention for gene knockdown NR1 subunit of N-methyl-D-aspartate (NMDA) receptor is designed according to the principle of RNA interference, and comprise homologous RNA sequence to NR1 subunit of NMDA receptor. It is demonstrated that the shRNA of the present invention targets to NR1 subunit of NMDA receptor and specifically suppresses the genetic expression of NR1 subunit in a dose-depended manner, so that a chemicals-induced nociception on skin can be efficiently relieved when it is subcutaneously delivered. The shRNA of the present invention comprise a first fragment, a connecting fragment and a second fragment, sequentially arranged from 5' end to 3' end, wherein sequences in the first fragment are homologous to that of NR1 subunit of NMDA receptor in a living organism, sequences in the second fragment are complementary to that of the first fragment, and sequences in the connecting fragment can be any nucleotides in repeated arrangement. The shRNA of the present invention can be synthesized by directly using a commercial RNA preparation kit or be expressed from plasmids or viral vectors.

In the preferable embodiment of the present invention, two target sequences, set forth in SEQ ID NO: 1 and 2 individually, are selected from GenBank accession number U-11418, which share homologous sequences among NR1 subunit of NMDA receptor in rats. Next, two oligonucleotides, named NR1-1 shRNA and NR1-2 shRNA, comprising the sense and antisense target sequences separated by a connecting fragment are synthesized and recorded as SEQ ID NO: 3 and 4 respectively. The connecting fragment can be any nucleotide including adenine, thymidine, cytimidine, guanine, or other modified base. Precisely, the target sequences have twenty-one nucleotides, and the connecting fragment preferably contains nine nucleotides in repeated arrangement. Then, the two oligonucleotides are sequentially subcloned into a commercial vector, for stable and sustainable expression of shRNAs of the present invention. In the present embodiment, the commercial vector is but not limit to a pSilencer 4.1-cytomegalomavirus (CMV) hygro vector (Ambion; Austin).

With such arrangement, the CMV vector encoded shRNAs of the present invention can be successfully delivered into nucleus and persistently transcribed by a RNA polymerase III in cells, with the sense and antisense target sequences binding with each other and bending in the form of a hairpin. Accordingly, the shRNAs of the present invention will be sustainedly expressed in cells so as to long-term silence NR1 subunit of NMDA receptor expression.

As described above, the shRNAs of the present invention can specifically and long-term inhibit the post-transcriptional expression of the NR1 subunit of NMDA receptor, as well as the normal function thereof.

For further evidencing the function of the shRNAs of the present invention, the CMV vector encoded NR1-1 and NR1-2 shRNAs (SEQ ID NO: 3 and 4) are delivered to animal model systems respectively, in order to study the pain response and the post-transcriptional gene silencing of NR1 in living organisms on formalin-induced nociception.

In the present embodiment, Sprangue-Dawley rats (SD rats), 250 g to 350 g in weight, are prepared and housed at a standard laboratory environment for undergoing three steps of shRNAs studies including (a) shRNAs study, (b) dose-effect study and (c) time course study. The above CMV vector encoded shRNAs of the present invention are subcutaneously injected to the SD rats with an acceptable vehicle under various conditions, and the flinch response and NR1 expression of the SD rats in the three steps of studies are monitored and summarized in the following paragraphs.

(a) shRNA Study:

With reference to Table 1, the SD rats are randomly assigned to four groups including (a1) vehicle group, (a2) saline group, (a3) NR1-1 group and (a4) NR1-2 group. The first injection is administered seven days before the formalin injection (known as the second injection), by subcutaneously injecting 2 μL polyethyleneimine (PEI), 100 μL saline and 10 μg CMV vector encoded NR1-1 shRNA and NR1-2 shRNA in one paw of rats in (a1) to (a4) groups respectively. The second injection is performed on the same paw of rats, with 1% formalin. Then, a flinching test and tissue dissection are carried out right after the second injection, for immediately analyzing rats' pain response and NR1 expression by real-time polymerase chain reaction (PCR) and western blotting. In the present embodiment, 10 μg of the CMV vectors encoded shRNAs, including NR1-1 and NR1-2 shRNAs, are mixed with 2 μL PEI (Fermentas Inc. Glen; Burnie) and further adjusted to 100 μl by 5% dextrose solution for convenient injection.

TABLE 1

Groups assignment in the (a) shRNAs study

| groups | First injection | | Second injection | |
|--------|-----------------|------|------------------|--------|
|        | agents          | dose | agents           | dose   |
| a1     | polyethyleneimine | 2 μL   | 1% formalin | 50 μL |
| a2     | saline            | 100 μL | 1% formalin | 50 μL |
| a3     | NR1-1 shRNA       | 10 μg  | 1% formalin | 50 μL |
| a4     | NR1-2 shRNA       | 10 μg  | 1% formalin | 50 μL |

Referring to FIG. 1a, the formalin-induced flinching response in the SD rats of the groups (a1) to (a4) is shown, wherein two phases of nociceptive behavior, including acute phase and tonic phase, in the SD rats can be clearly observed on rats after formalin-injection. As it is indicated in curves (a1) to (a4), the flinching behavior of the acute phase begins immediately after the second injection (1% formalin) and lasts for three to five minutes. Furthermore, the flinching behavior of the tonic phase starts at about fifteenth to twentieth minutes after the formalin-injection and lasts for twenty to forty minutes. In comparison, the curve (a3) and (a4) points out that the flinching behavior both in the acute phase and in the tonic phase turns minor on the SD rats of the groups (a3) and (a4). It is suggested that the SD rats had the CMV viral DNA encoding shRNAs treatment only show mild pain response on formalin-induced nociception.

To examine the silencing function of the shRNAs of the present invention, real time PCR and western blotting are used for analyzing the NR1 expression in the groups (a1) to (a4). In the present embodiment, total RNA samples of the SD rats of the four groups are collected and purified by using a total RNA mini kit (Geneaid Biotech Ltd; Sijhih City), followed by being reverse transcriptased by a DNA reverse transcription kit (Applied Biosystems Inc; Foster City) and analyzed by an ABI prism 7500 sequence detection system (Applied Biosystems Inc; Foster City). In the present embodiment, specific primer pairs including NR1 set forth in SEQ ID NO: 5 and 6, NR2A set forth in SEQ ID NO: 7 and 8, NR2B set forth in SEQ ID NO: 9 and 10, NR2C set forth in SEQ ID NO: 11 and 12, NR2D set forth in SEQ ID NO: 13 and 14, and α-interferon set forth in SEQ ID NO: 15 and 16 are designed and used in the real time PCR program for detecting the mRNA expression of the NR1, NR2A, NR2C, NR2D and α-interferon in the SD rats of the four groups.

Figure 1B:
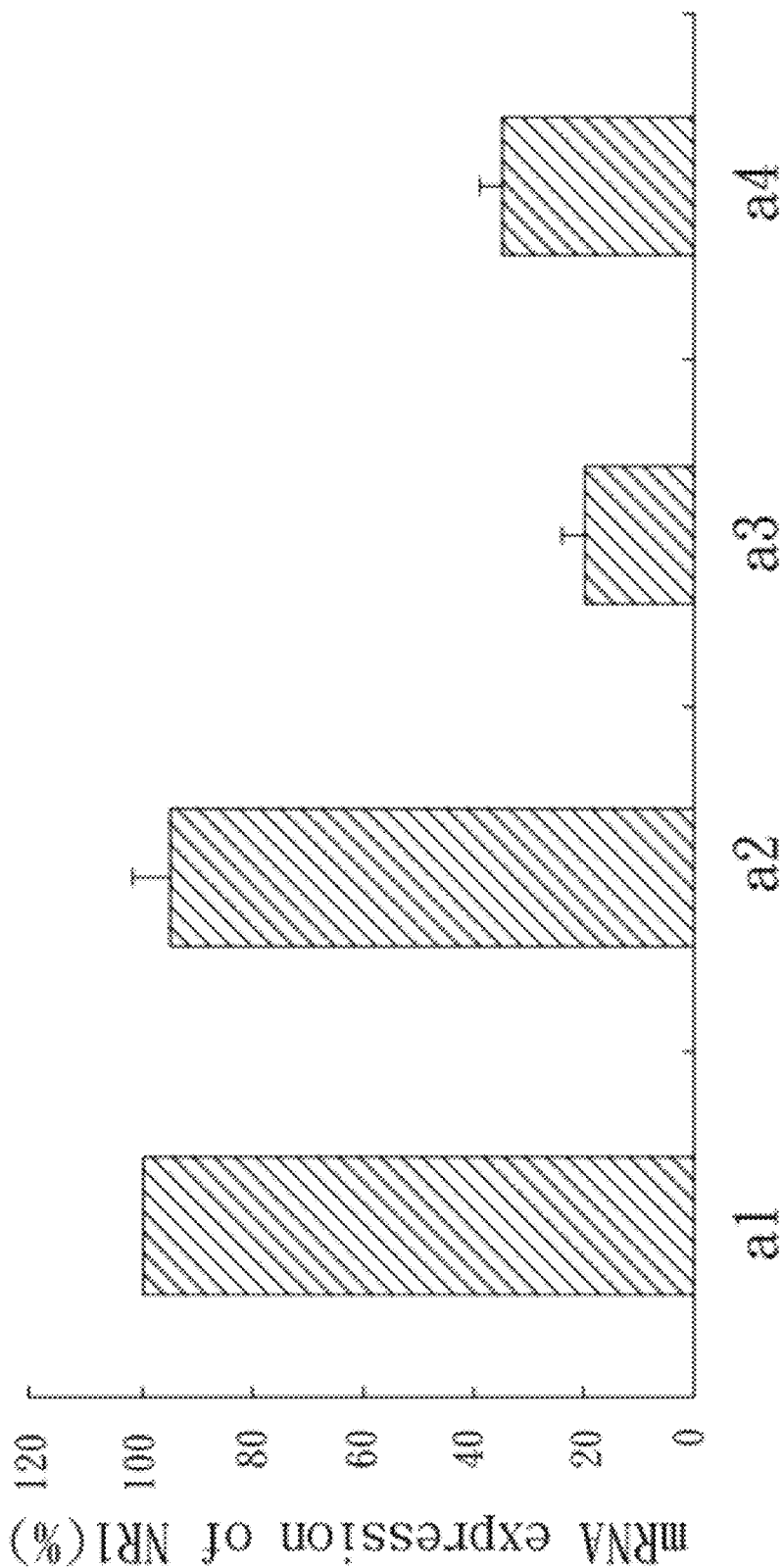
FIG. 1b is a bar chart showing mRNA expression of NR1 in rats after subcutaneous injection of NR1 shRNA.

Referring to FIG. 1b, the mRNA expression of NR1 on rats in each group is shown, wherein the NR1 expression is significantly lower in the groups (a3) and (a4) than in the groups (a1) and (a2). In comparison with the NR1 expression in the group (a1), as it is defined as 100% of mRNA expression, the SD rats in the groups (a3) and (a4) only have 20% and 37% of mRNA expression. It is noted that the mRNA expression in the SD rats is dramatically suppressed by the vector-encoded shRNAs of the present invention.

It is believed that the shRNAs of the present invention is designed according to the target sequences derived from NR1 subunit of NMDA in a living organism, so that the shRNAs are capable of targeting to the NR1 subunit of NMDA and silencing the post-transcriptional gene expression. Therefore, the normal functions of the NR1 subunit of NMDA receptor, such as pain sensitization, are also interrupted.

(b) Dose-Effect Study:

With reference to Table 2, the SD rats were randomly assigned to 6 different groups including (b1) saline group, (b2) vehicle group, (b3) NR1-3 group, (b4), (b5) and (b6) groups, with subcutaneous injection of 100 saline, 2 μl PEI, 10 μg CMV vector encoded NR1-3 shRNA, and 5 μg, 10 μg and 20 μg CMV vector encoded NR1-1 shRNA respectively. The NR1-3 shRNA is a mismatched shRNA of the NR1 subunit of NMDA receptor, which shows no homology with the target sequence of the present invention and is set forth in SEQ ID NO: 17. Similar to the processes in the (a) shRNAs study, the first injection is administered on one paw of the SD rats of each group seven days prior than the second injection, giving formalin to the same paw of the SD rats. Also, the flinching test and tissue dissection are also performed on the SD rats of the six groups after the second injection, for immediately analyzing rats' pain response and NR1 expression.

TABLE 2

Groups assignment in the (b) dose-effect study

| groups | First injection | | Second injection | |
|---|---|---|---|---|
| | agents | dosage | agents | dosage |
| b1 | saline | 100 μL | 1% formalin | 50 μL |
| b2 | PEI | 2 μL | 1% formalin | 50 μL |
| b3 | NR1-3 shRNA | 10 μg | 1% formalin | 50 μL |
| b4 | NR1-1 shRNA | 5 μg | 1% formalin | 50 μL |
| b5 | NR1-1 shRNA | 10 μg | 1% formalin | 50 μL |
| b6 | NR1-1 shRNA | 20 μg | 1% formalin | 50 μL |

Figure 2A:
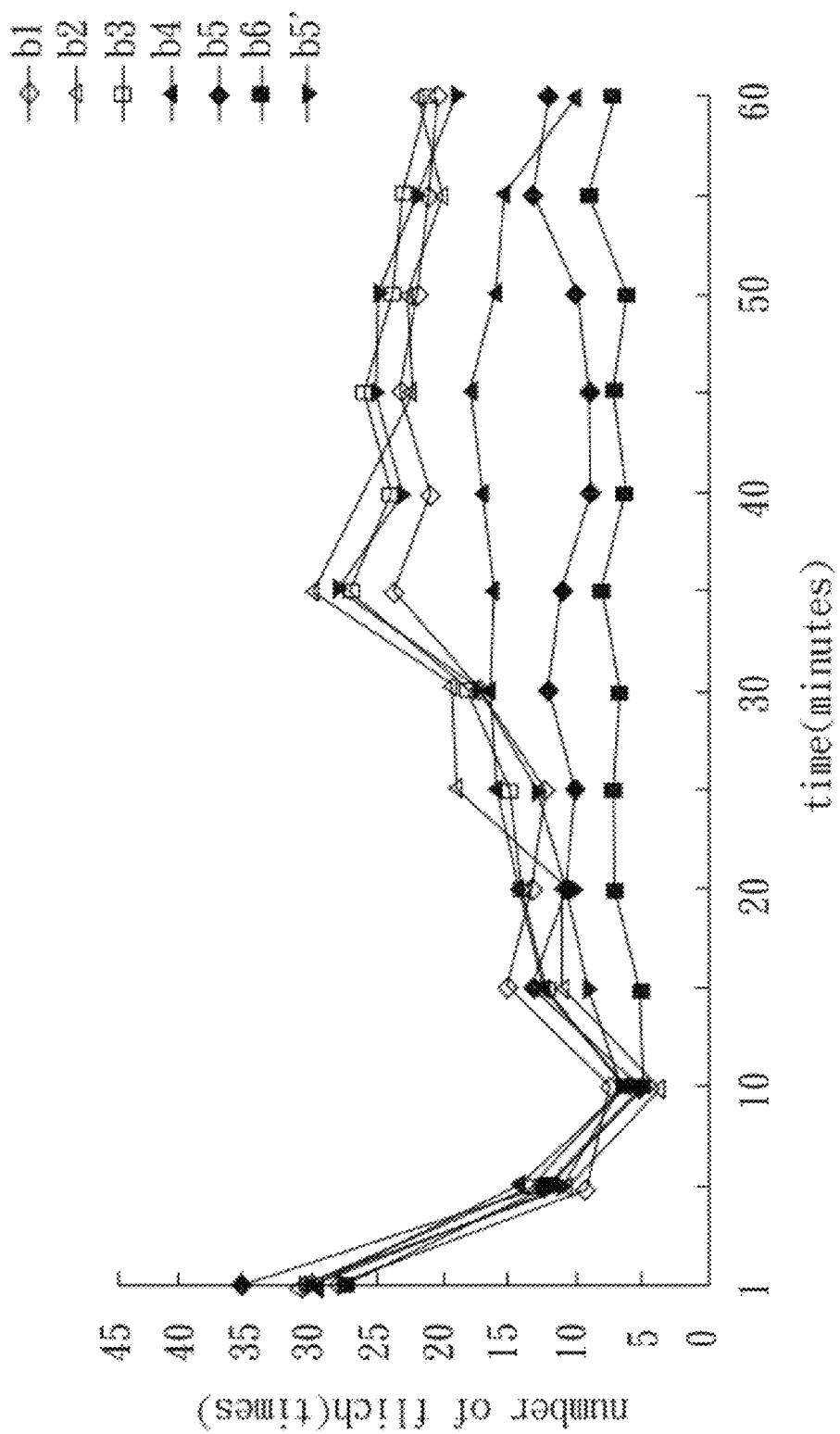
FIG. 2a is a line chart illustrating data of flinches response in rats on formalin-induced nociception.

Referring to the FIG. 2a, the formalin-induced flinching response in the SD rats of the groups (b1) to (b6) is shown, wherein a curve (b5') indicates the flinching data of the SD rats of the group (b5) that have formalin injection on their contralateral paw. The curves (b4), (b5) and (b6) shows that, number of flinch in the SD rats decreases dramatically, especially for the SD rats in the groups (b4) and (b5). However, according to curves (b1), (b2), (b3) and (b5'), no significant decrease in the number of flinches has been noticed in rats received formalin injection on their contralateral paw or had saline, PEI and the mismatched shRNA treatment. It is suggested that, the antinociceptive effect of the shRNA of the present invention is in a dose-depended manner, and is localized at where it is delivery rather than systemic.

Figure 2B:
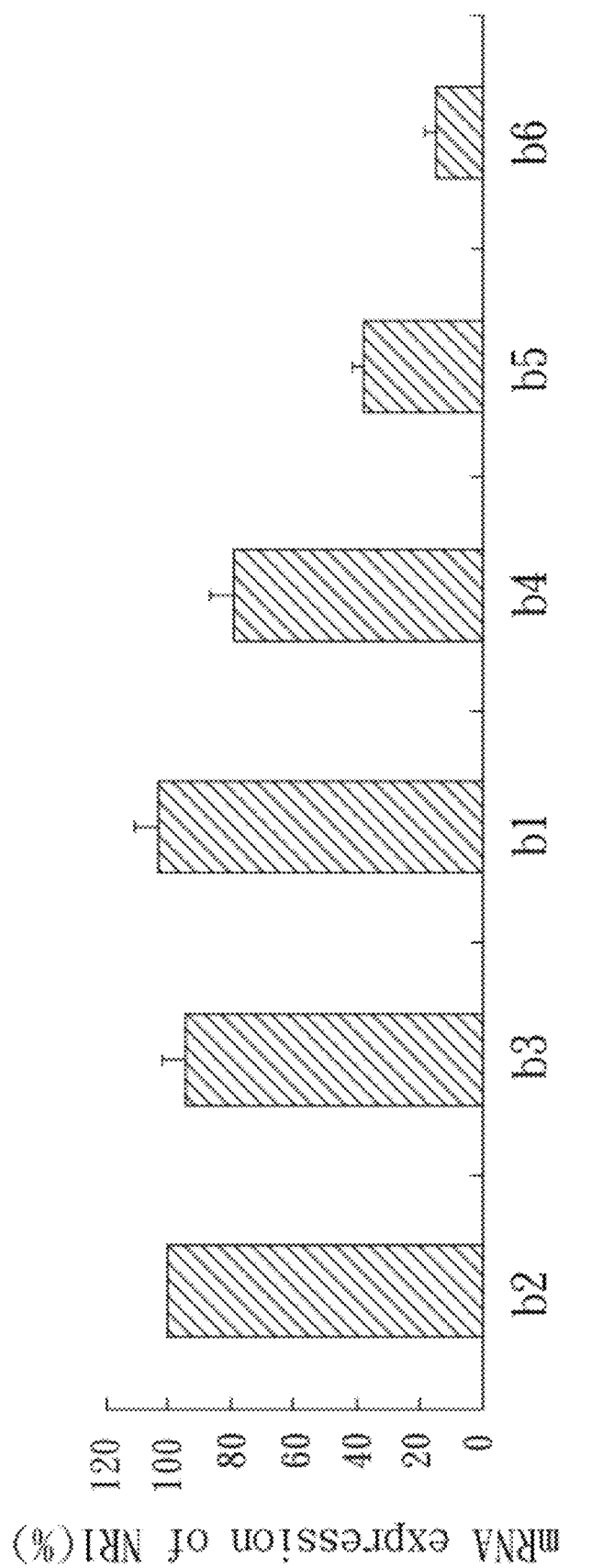
FIG. 2b is a bar chart showing mRNA expression of NR1 in rats after subcutaneous injection of NR1 shRNA.

Referring to FIG. 2b, the mRNA expression of NR1 in each group is shown, wherein the NR1 expression is significantly lower in the groups (b5) and (b6) than in the groups (b1) to (b3). In comparison with the NR1 expression in the group (b1), which is defined as 100% of mRNA expression, the SD rats in the groups (b5) and (b6) only have 40% and 17% of mRNA expression. It is indicated that the silenced NR1 expression on rats carried out by the vector encoded shRNA of the present invention is in accordance with a dose-depended manner.

Figure 2C:
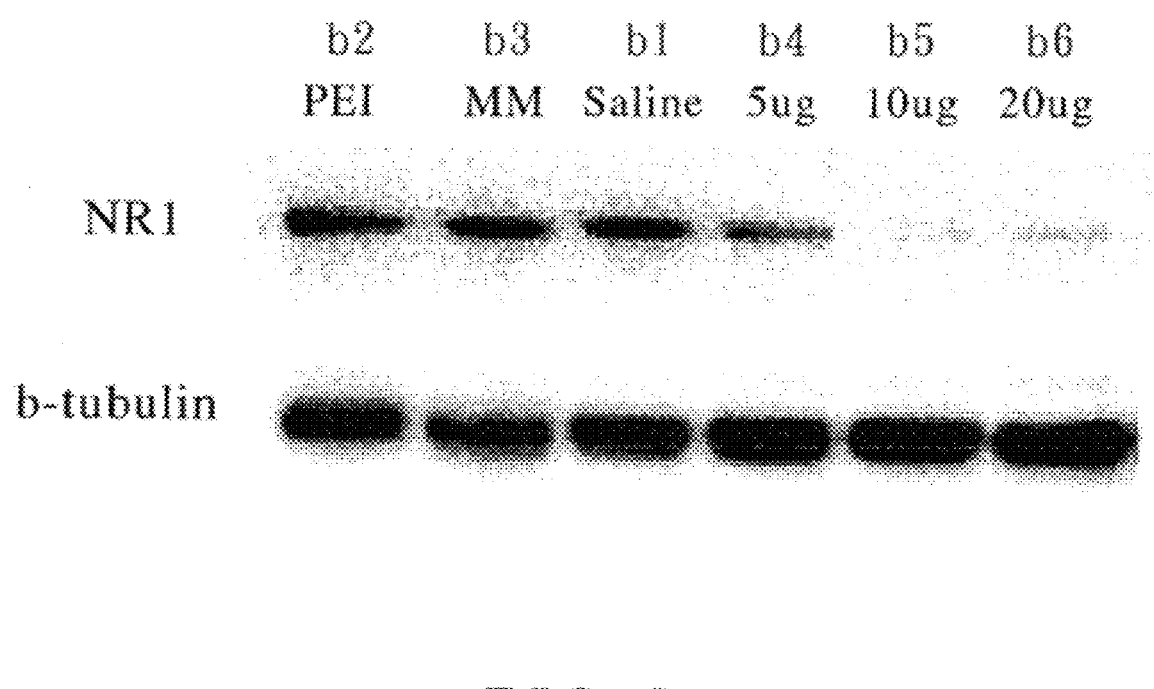
FIG. 2c is a western blot photograph showing protein expression of NR1 in rats after subcutaneous injection of NR1 shRNA.
Figure 2D:
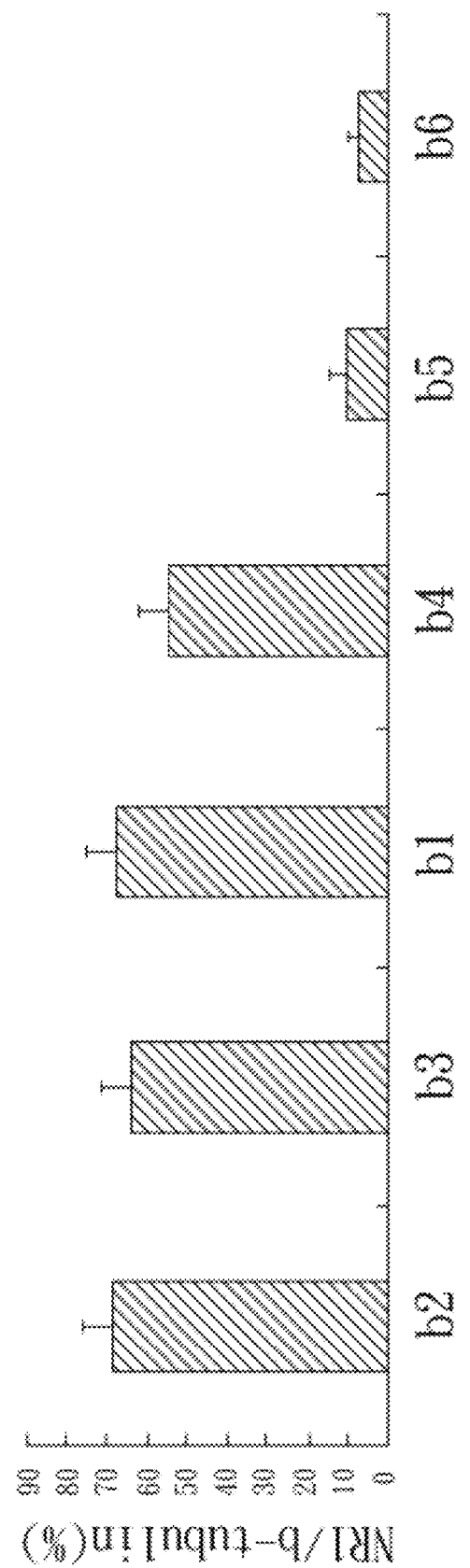
FIG. 2d is a bar chart illustrating protein expression of NR1 in rats after subcutaneous injection of NR1 shRNA.

Referring to FIGS. 2c and 2d, the protein expression of NR1 in each group is shown, wherein the FIG. 2c is a western blot photo and the FIG. 2d shows the immunoreactivity ratio between the NR1 and β-tubulin on the SD rats of the six groups. In the present embodiment, total protein samples of the SD rats in each group are taken from their skin tissues and prepared by 20 times diluting in a tissue protein extraction reagent (PIERCE; Rockford) containing 25 mM bicine, 150 mM sodium chloride (pH 7.6), protease inhibitors, 100 mM 4-(2-Aminoethyl)benzenesulfonyl fluoride hydrochloride, 80 M aprotinin, crystalline, 5 mM bestatin, 1.5 mM E-64, protease inhibitor, 2M leupeptin and 1 mM pepstatin A. Then, the total protein samples are homogenized with a homogenizer and centrifuged at 12,000 rpm/min for 30 min at 4° C. to collect supernatant. The supernatant are sequentially assayed by a Quant-iT™ protein assay kit (Invitrogen; Carlsbad) and electrophoresed on a 10% sodium dodecylsulfate polyacrylamide gel. Next, the electrophoresed data are transferred to a polyvinylidine fluoride membrane and blocked with 5% nonfat dry milk, ready for the following western blot program. During the western blot, the primary antibody, a 2000 times diluted rabbit polyclonal anti-glutamate receptor NR1 (Sigma; Mo.), and the secondary antibody, a 5000 times diluted horseradish peroxidase-coupled goat anti-rabbit immunoglobulin G (Chemicon; Billerica), are prepared and co-incubate with the polyvinylidine fluoride membrane at a suitable temperature, for example 4° C. or room temperature. Finally, the polyvinylidine fluoride membrane is developed by a western blot chemiluminescence reagent plus (Millipore; Billerica) to obtain the western blot data of the present invention. Additionally, for further densitometry the protein analyses, the western blot data are scanned and quantified by an Image-Pro® plus analysis software (MediaCybernetics; Silver Spring) in the present embodiment.

With reference to FIGS. 2c and 2d, it is obvious that the protein expression of the NR1 significantly decreased in the SD rats of the groups (b5) and (b6). In comparison with the NR1 expression in the group (b1) with around 70% in the immunoreactivity ratio between NR1 and β-tubulin, the SD rats in the groups (b5) and (b6) only have 10% and less than 10% of protein expression. It is indicated that the NR1 expression in the SD rats is suppressed by the vector encoded shRNAs of the present invention in a dose-depended manner.

It is believed that, the antinociception of the shRNA of the present invention is localized and in a dose-depended manner. Generally, apply higher dose of the shRNA of the present invention will lead to stronger silencing effect on the target gene. Preferably, 10 μg of the viral encoded shRNA is used for persistently suppressing the target gene expression and the nociceptive response in living organisms.

(c) Time Course Study:

With reference to Table 3, the SD rats are randomly assigned into eight groups including (c1) vehicle group, (c2), (c3) vehicle group, (c4), (c5) vehicle group, (c6), (c7) vehicle group, (c8), (c9) vehicle group and (c10), with subcutaneous injection of 2 μL PEI or 10 μg viral vector encoded NR1-1 shRNA 3, 7, 14, 21 or 28 days prior than the second injection. In the (c) time course study, the groups (c1, c3, c5, c7 and c9) are served as controls. The same as the procedure in the (a) shRNAs study and the (b) dose-effect study, the flinching test and the tissue dissection are also carried out on the SD rats of the eight groups after the formalin injection for timely analyzing rats' pain response and NR1 expression.

TABLE 3

Group assignment in the time course study

| groups | First injection | | | Second injection | |
|---|---|---|---|---|---|
| | agents | time | dose | agents | dose |
| c1 | PEI | 3 days | 2 µL | 1% formalin | 50 µL |
| c2 | NR1-1 shRNA | 3 days | 10 µg | 1% formalin | 50 µL |
| c3 | PEI | 7 days | 2 µL | 1% formalin | 50 µL |
| c4 | NR1-1 shRNA | 7 days | 10 µg | 1% formalin | 50 µL |
| c5 | PEI | 14 days | 2 µL | 1% formalin | 50 µL |
| c6 | NR1-1 shRNA | 14 days | 10 µg | 1% formalin | 50 µL |
| c7 | PEI | 21 days | 2 µL | 1% formalin | 50 µL |
| c8 | NR1-1 shRNA | 21 days | 10 µg | 1% formalin | 50 µL |
| c9 | PEI | 28 days | 2 µL | 1% formalin | 50 µL |
| c10 | NR1-1 shRNA | 28 days | 10 µg | 1% formalin | 50 µL |

Figure 3A:
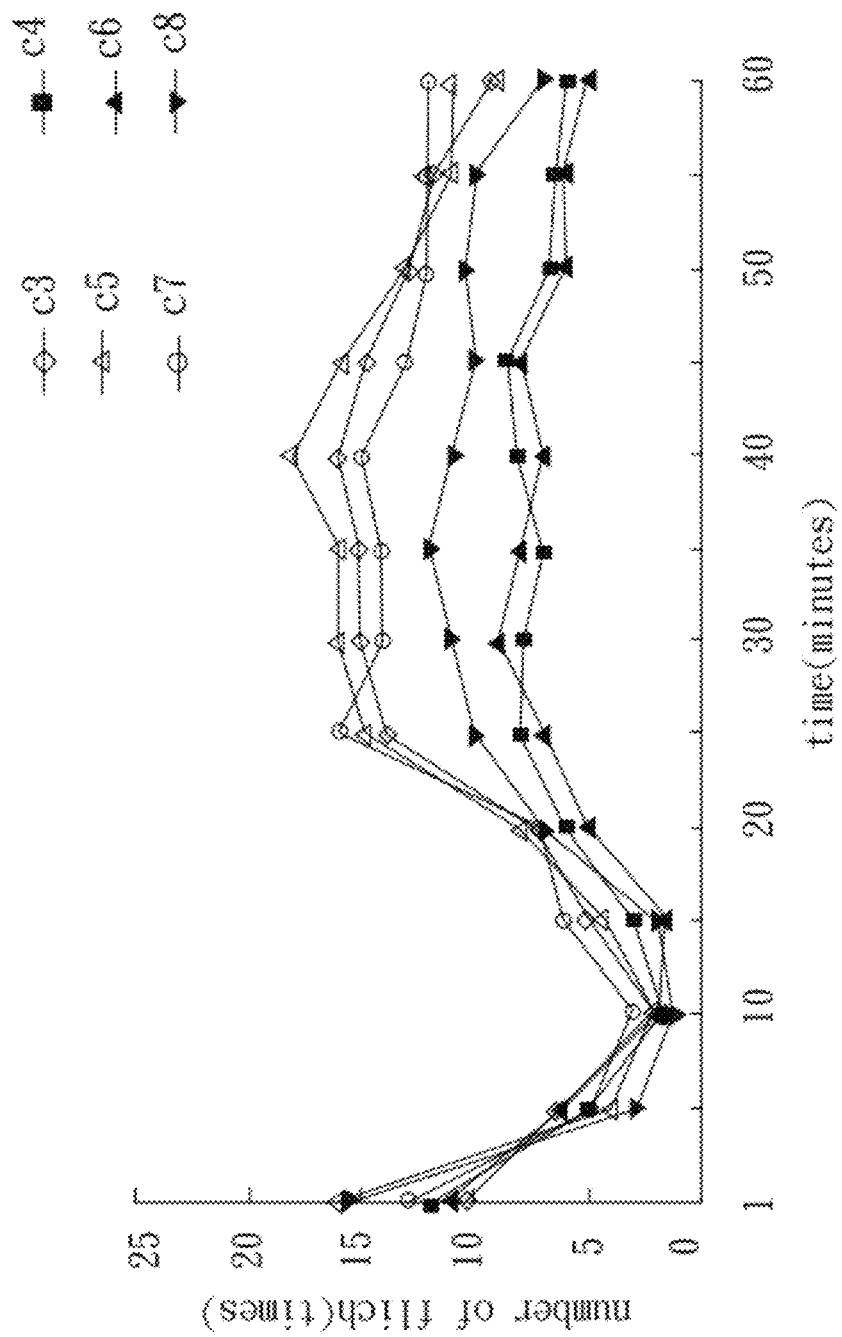
FIG. 3a is a line chart illustrating data of flinches response in rats on formalin-induced nociception.

Referring to the FIG. 3a, the formalin-induced flinching response in the SD rats of the eight groups are summarized, wherein curves (c1), (c2), (c9) and (c10) showing number of flinch in the SD rats of the groups (c1), (c2), (c9) and (c10) are excluded from it. It is noticed that number of flinch decreases significantly on rats of the groups (c4) and (c6). Moreover, as shown in curve (c8), number of flinch decrease at the twenty-fifth and the fortieth minutes after the formalin-induced nociception in rats of the group (c8). It is suggested that the antinociceptive effect on living organisms caused by the shRNA of the present invention is persistent and mainly lasts for seven to twenty-one days.

Figure 3C:
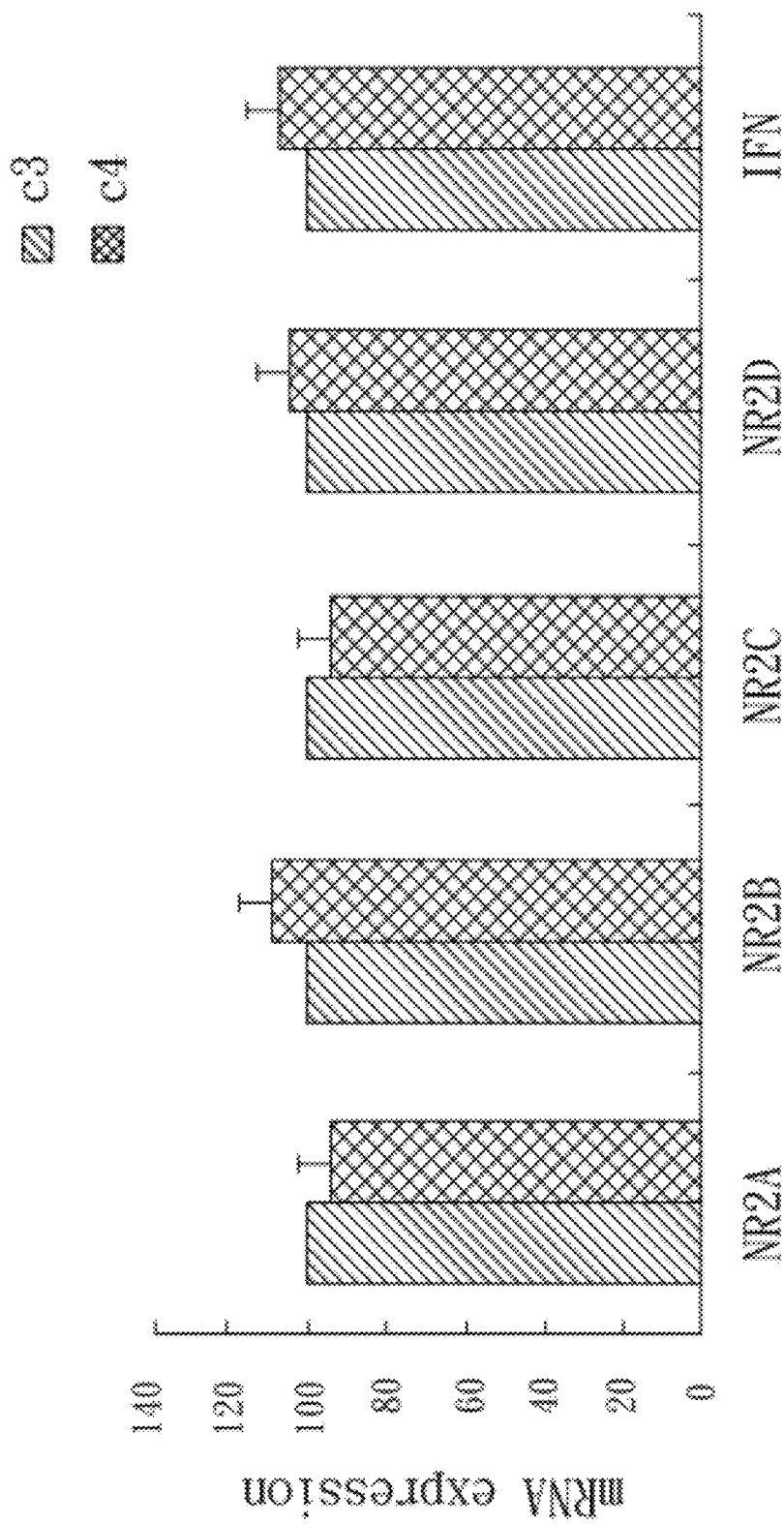
FIG. 3c is a bar chart illustrating mRNA expression of NR2A, NR2B, NR2C, NR2D and α-interferon in rats after subcutaneous injection of NR1 shRNA.

Referring to FIGS. 3b and 3c the mRNA expression of NR1 in each group, as well as the mRNA expression of NR2A, NR2B, NR2C, NR2D and α-interferon is shown. It is indicated that a dramatically decrease in the mRNA expression of NR1 is noted on the seventh and fourteenth days after injection of the vector encoded NR1-1 shRNA. Furthermore, no silence gene expression is further observed on NR2A, NR2B, NR2C, NR2D and α-interferon. It is believed that, the silenced gene expression caused by the shRNA of the present invention is specific to the NR1 subunit of NMDA receptor.

Figure 3D:
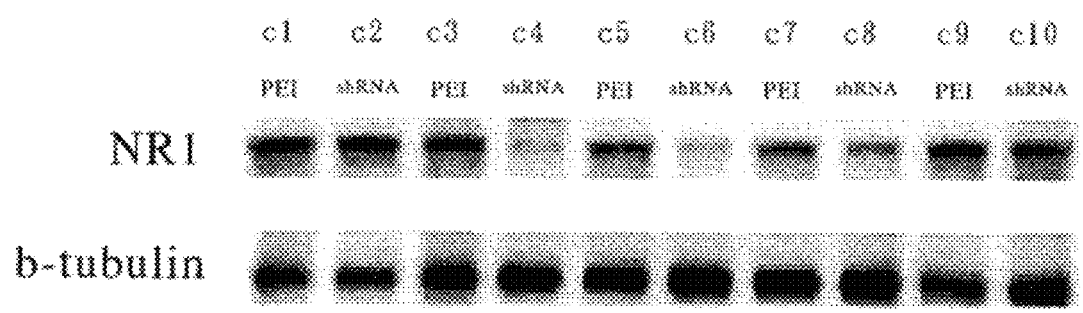
FIG. 3d is a western blot photo showing protein expression of NR1 in rats after subcutaneous injection of NR1 shRNA.
Figure 3E:
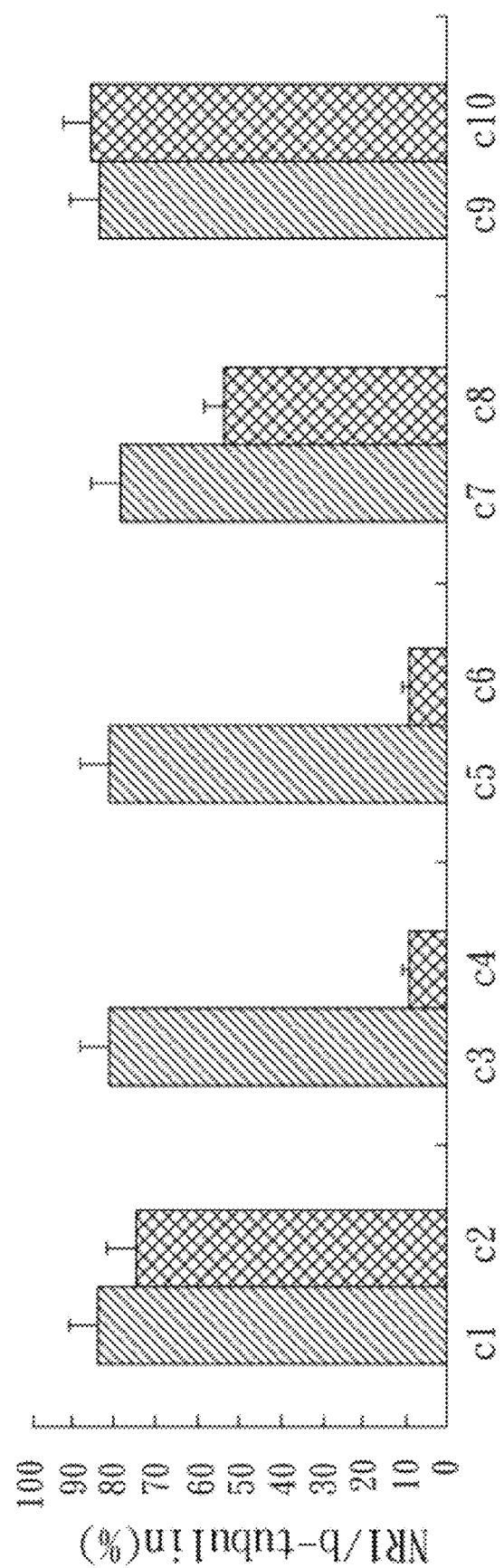
FIG. 3e is a bar chart illustrating protein expression of NR1 in rats after subcutaneous injection of NR1 shRNA.

Referring to FIGS. 3d and 3e, the protein expression of NR1 on rats of each group is shown. It is noted that a dramatically decrease in the NR1 expression is observed on the seventh and fourteenth days after injection of the vector encoded NR1-1 shRNA. Hence, the silence NR1 expression caused by the shRNA of the present invention is persistent and lasts for seven to twenty-one days.

In summary, it is proved that the shRNAs of the present invention shows long-termed and specifically antinociceptive effect and silence NR1 expression on the living organism. Generally, the shRNAs-induced antinociception and silenced NR1 expression on the living organism will last for seven to twenty-one days in the present invention. Therefore, the shRNAs of the present invention will not cause any permanent disorders to the NR1 subunit of NMDA receptor in the living organism.

Through the present invention, two viral encode shRNAs are designed and prepared for specifically targeting to NR1 subunit of NMDA receptor in rats. The two CMV vector encoded shRNAs, including NR1-1 and NR1-2 shRNAs, show significantly antinociceptive effect and silenced NR1 expression in the living organism on formalin-induced nociception. According to the description in the (b) dose-effect study and the (c) time course study, the antinociception, as well as the silenced NR1 expression is carried out by the shRNAs of the present invention in a dose depended manner and mainly persisting seven to twenty-one days. Additionally, the silence of NR1 expression is specifically and will not be shown on other non-target genes, such as NR2A, NR2B, NR2C, NR2D and α-interferon.

Therefore, a new therapeutic approach for treating inflammatory pain is sufficient to be developed according to the shRNAs of the present invention, by providing the vector encoded NR1-1 and NR1-2 shRNAs via subcutaneous injection to a target living organism to specifically and persistently suppress the gene expression of NR1 subunit of NMDA receptor. With such approach, the chronic and acute pain response on the living organism can be temporary reduced. The vector encoded NR1-1 and NR1-2 shRNAs of the present invention is preferably to be delivered to the living organism every seven to twenty-one days, at a dose of 10 µg to 20 µg. Furthermore, the NR1-1 and NR1-2 shRNAs are preferably to be applied on where it affected due to the NR1-1 and NR1-2 shRNAs induced local antinociception.

Additionally, an analgesic based on the NR1-1, NR1-2 shRNAs of the present invention is potential to be developed and applied to clinical medicine for treating pathological pain, which comprises the NR1-1 or NR1-2 shRNA, and an acceptable vehicle for the shRNA. The acceptable vehicle can be polyethyleneimine (PEI) or any other acceptable reagents. Preferably, the analgesic is used at a dose of 10 µg to 20 µg, and delivered to the target every seven to twenty-one days via subcutaneous injection. The analgesic can be in the form of a liquid medicine for subcutaneous injection or ointment. Generally, the analgesic can be given to patients individually or combined with other acceptable medicaments, for providing sustaining and localized anti-pain effect on patients.

Although the invention has been described in detail with reference to its presently preferred embodiment, it will be understood by one of ordinary skill in the art that various modifications can be made without departing from the spirit and the scope of the invention, as set forth in the appended claims.

What is claimed is:

1. A short hairpin RNA comprising:
a first fragment sharing homologous nucleotides amount NR1 subunit of N-methyl-D-aspartate (NMDA) receptor for gene knockdown the genetic expression of the NR1 subunit of NMDA; a second fragment having complementary sequence to the first fragment; and a connecting fragment having any base in repeated arrangement, and connecting to the first and second fragments, wherein the short hairpin RNA is encoded in a sequence set forth in SEQ ID No: 3.

2. A short hairpin RNA comprising:
a first fragment sharing homologous nucleotides among NR1 subunit of N-methyl-D-aspartate (NMDA) receptor for gene knockdown the genetic expression of the NR1 subunit of NMDA; a second fragment having complementary sequence to the first fragment; and a connecting fragment having any base in repeated arrangement, and connecting to the first and second fragments, wherein the short hairpin RNA is encoded in a sequence set forth in SEQ ID No: 4.

3. An analgesic drug for skin inflammation pain comprising:
a short hairpin RNA; and an acceptable vehicle for the short hairpin RNA, wherein the short hairpin RNA is encoded in sequences set forth in SEQ ID No: 3 or 4.

4. The analgesic drug for skin inflammation pain as defined in claim 3, wherein the short hairpin RNA is in the form of a vector expressed short hairpin RNA.

5. The analgesic drug for skin inflammation pain as defined in claim 3, with the short hairpin RNA at a dose of 5 μg to 20 μg.

6. The analgesic drug for skin inflammation pain as defined in claim 3, wherein the acceptable vehicle for the short hairpin RNA is polyethyleneimine.

7. The analgesic drug for skin inflammation pain as defined in claim 3, with the ratio of the short hairpin RNA to the acceptable vehicle: 1 μg short hairpin RNA to 0.2 μl vehicle.

8. A method of treatment for pathological pain, by applying a short hairpin RNA to subcutaneous tissues of living organisms for gene knockdown the genetic expression of NR1 subunit of NMDA receptor in hypoderm, wherein the short hairpin RNA is encoded in sequences set forth in SEQ ID No: 3 or 4.

9. The method of treatment for pathological pain as defined in claim 8, wherein the short hairpin RNA is in the form of a vector expressed short hairpin RNA.

10. The method of treatment for pathological pain as defined in claim 8, with the short hairpin RNA at a dose of 5 μg to 20 μg.

11. The method of treatment for pathological pain as defined in claim 8, wherein the short hairpin RNA is applied every seven to twenty-one days to the living organisms.

12. The method of treatment for pathological pain as defined in claim 8, wherein the vector is selected from a group of plasmids and viral vectors.

* * * * *

SEQUENCE LISTING

<160> NUMBER OF SEQ ID NOS: 17

<210> SEQ ID NO 1
<211> LENGTH: 21
<212> TYPE: DNA
<213> ORGANISM: Mus musculus

<400> SEQUENCE: 1
aaaccaggcc aataagcgac a                     21

<210> SEQ ID NO 2

```
<211> LENGTH: 21
<212> TYPE: DNA
<213> ORGANISM: Mus musculus

<400> SEQUENCE: 2
aatgtccatc tactctgaca a                                              21

<210> SEQ ID NO 3
<211> LENGTH: 51
<212> TYPE: DNA
<213> ORGANISM: Artificial Sequence
<220> FEATURE:
<223> OTHER INFORMATION: Synthetic oligonucleotide with sense and
      antisense sequence from GenBank accession number U-11418
<220> FEATURE:
<221> NAME/KEY: misc_feature
<222> LOCATION: (22)..(30)
<223> OTHER INFORMATION: n is a, c, g, or t

<400> SEQUENCE: 3
aaaccaggcc aataagcgac annnnnnnnn tgtcgcttat tggcctggtt t              51

<210> SEQ ID NO 4
<211> LENGTH: 51
<212> TYPE: DNA
<213> ORGANISM: Artificial Sequence
<220> FEATURE:
<223> OTHER INFORMATION: Synthetic oligonucleotide with sense and
      antisense sequence from GenBank accession number U-11418
<220> FEATURE:
<221> NAME/KEY: misc_feature
<222> LOCATION: (22)..(30)
<223> OTHER INFORMATION: n is a, c, g, or t

<400> SEQUENCE: 4
aatgtccatc tactctgaca annnnnnnnn ttgtcagagt agatggacat t              51

<210> SEQ ID NO 5
<211> LENGTH: 17
<212> TYPE: DNA
<213> ORGANISM: Artificial Sequence
<220> FEATURE:
<223> OTHER INFORMATION: Synthetic  Oligonucleotide Primer

<400> SEQUENCE: 5
gcgactcccg cagcaat                                                   17

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 6
cccctgccat gttctcaaaa                                                20

<210> SEQ ID NO 7
<211> LENGTH: 26
<212> TYPE: DNA
<213> ORGANISM: Artificial Sequence
<220> FEATURE:
<223> OTHER INFORMATION: Synthetic  Oligonucleotide Primer

<400> SEQUENCE: 7
tccactcaag gaatcttgtg agatat                                         26

<210> SEQ ID NO 8
```

```
<211> LENGTH: 26
<212> TYPE: DNA
<213> ORGANISM: Artificial Sequence
<220> FEATURE:
<223> OTHER INFORMATION: Synthetic Oligonucleotide Primer

<400> SEQUENCE: 8
acttgcccat gtgtatttat ttgttt                                          26

<210> SEQ ID NO 9
<211> LENGTH: 17
<212> TYPE: DNA
<213> ORGANISM: Artificial Sequence
<220> FEATURE:
<223> OTHER INFORMATION: Synthetic Oligonucleotide Primer

<400> SEQUENCE: 9
aaccctcgtg gccgaca                                                    17

<210> SEQ ID NO 10
<211> LENGTH: 18
<212> TYPE: DNA
<213> ORGANISM: Artificial Sequence
<220> FEATURE:
<223> OTHER INFORMATION: Synthetic Oligonucleotide Primer

<400> SEQUENCE: 10
ggtggacaga tgcgggaa                                                   18

<210> SEQ ID NO 11
<211> LENGTH: 21
<212> TYPE: DNA
<213> ORGANISM: Artificial Sequence
<220> FEATURE:
<223> OTHER INFORMATION: Synthetic Oligonucleotide Primer

<400> SEQUENCE: 11
ggcccagctt ttgaccttag t                                               21

<210> SEQ ID NO 12
<211> LENGTH: 19
<212> TYPE: DNA
<213> ORGANISM: Artificial Sequence
<220> FEATURE:
<223> OTHER INFORMATION: Synthetic Oligonucleotide Primer

<400> SEQUENCE: 12
cctgtgacca ccgcaagag                                                  19

<210> SEQ ID NO 13
<211> LENGTH: 22
<212> TYPE: DNA
<213> ORGANISM: Artificial Sequence
<220> FEATURE:
<223> OTHER INFORMATION: Synthetic Oligonucleotide Primer

<400> SEQUENCE: 13
agggtttctg cattgcccca tt                                              22

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 14
```

```
tcaccaatca tgccattcca                                                    20

<210> SEQ ID NO 15
<211> LENGTH: 19
<212> TYPE: DNA
<213> ORGANISM: Artificial Sequence
<220> FEATURE:
<223> OTHER INFORMATION: Synthetic Oligonucleotide Primer

<400> SEQUENCE: 15
cttggctgtt tgccccatt                                                     19

<210> SEQ ID NO 16
<211> LENGTH: 21
<212> TYPE: DNA
<213> ORGANISM: Artificial Sequence
<220> FEATURE:
<223> OTHER INFORMATION: Synthetic Oligonucleotide Primer

<400> SEQUENCE: 16
cgtgacagta gctgcggttc c                                                  21

<210> SEQ ID NO 17
<211> LENGTH: 51
<212> TYPE: DNA
<213> ORGANISM: Artificial Sequence
<220> FEATURE:
<223> OTHER INFORMATION: Synthetic oligonucleotides with sense and
      antisense sequence
<220> FEATURE:
<221> NAME/KEY: misc_feature
<222> LOCATION: (22)..(30)
<223> OTHER INFORMATION: n is a, c, g, or t

<400> SEQUENCE: 17
aaaccagcgc aataacggac annnnnnnnn tgtccgttat tgcgctggtt t                 51
```